(12) United States Patent
Morizur et al.

(10) Patent No.: US 8,202,960 B1
(45) Date of Patent: Jun. 19, 2012

(54) BISPHENOL COMPOUNDS AND METHODS OF MAKING

(75) Inventors: Jean-Francois Morizur, Evansville, IN (US); Swaminathan Shubashree, Bangalore (IN)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 0 days.

(21) Appl. No.: 13/154,748

(22) Filed: Jun. 7, 2011

(51) Int. Cl.
*C08G 64/00* (2006.01)
*C08G 63/02* (2006.01)

(52) U.S. Cl. ........ 528/196; 528/198

(58) Field of Classification Search .......... 528/196, 528/198
See application file for complete search history.

(56) References Cited

U.S. PATENT DOCUMENTS

| | | |
|---|---|---|
| 2009/0124749 A1 | 5/2009 | Steendam et al. |
| 2010/0130700 A1 | 5/2010 | de Brouwer et al. |
| 2011/0060106 A1 | 3/2011 | de Kraker et al. |

*Primary Examiner* — Terressa Boykin
(74) *Attorney, Agent, or Firm* — Venable LLP; Keith G. Haddaway; Michael E. Nelson

(57) ABSTRACT

Disclosed are bisphenol compounds, such as tetramethylcyclobutane diol-bisphenol, and processes for making and using them.

33 Claims, No Drawings

BISPHENOL COMPOUNDS AND METHODS OF MAKING

FIELD OF THE INVENTION

The present disclosure relates to compounds and processes for making and using them. In particular, the present disclosure relates to bisphenol compounds and methods of making them.

BACKGROUND OF THE INVENTION

In many cases, desirable properties can be imparted to polycarbonates and other polymers by reacting together one or more aromatic dihydroxy monomers via melt or interfacial polymerization process to form polycarbonate homopolymers and copolymers. In such cases, it is often desirable to obtain random incorporation of the monomers along the polymeric backbone to achieve desirable physical properties. This can be difficult to achieve by melt or interfacial polymerization essentially due to the inherent difference in reactivity of the monomers. It becomes even more challenging when aromatic dihydroxy compounds are copolymerized with aliphatic diols which present, for example, secondary alcohols, such as for example cyclobutane diols, for which the pKa is greater than commonly use bisphenols. The efficient polymerization of such compounds involves a significant number of trade-offs. For example, one can compensate for low reactivity by altering the amount of catalyst introduced into the system, but the temperature and reaction time would lead inherently to lower optical properties of the final polymeric material (e.g. yellowness and transparency).

Thus it is clear that there is a need for compounds and methods of making them to convert cyclobutane diols, such as tetramethylcyclobutane diol (TMCBD) to bisphenols in order to improve their incorporation in final copolymers made thereby.

BRIEF DESCRIPTION

Disclosed, in various embodiments, are compounds and processes for making and using them. In a particular embodiment a process is provided for making a TMCBD-bisphenol that may be polymerized subsequently via interfacial reaction to form a polyester carbonate.

In describing the various embodiments below, it should be understood that any recited substituents can be combined with any other substituents. In some embodiments, a compound of Formula I is provided,

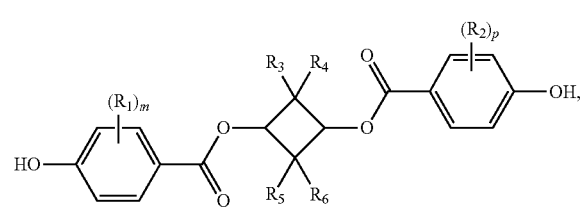

I wherein m and p are the same or different and are each an integer from 0-4, and each $R_1$ and $R_2$ are the same or different and are each independently selected from one or more of halogen, $C_1$-$C_{12}$ alkyl, $C_1$-$C_6$ aliphatic, $C_3$-$C_6$ cycloaliphatic, $C_1$-$C_{12}$ alkoxy, and $C_1$-$C_{12}$ alkyl ester, and $R_3$, $R_4$, $R_5$, and $R_6$ are the same or different and are each independently selected from one or more of hydrogen, and $C_1$-$C_2$ aliphatic. In some aspects, m may be 1, p may be 1, or m and p may be 0. In certain aspects, $R_3$, $R_4$, $R_5$, and $R_6$ may be each methyl.

In other embodiments, a compound of Formula Ia

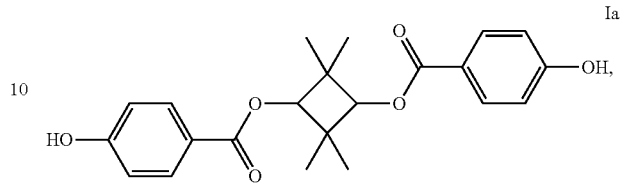

Ia is provided.

In other embodiments, a process is provided for preparing a compound of Formula I

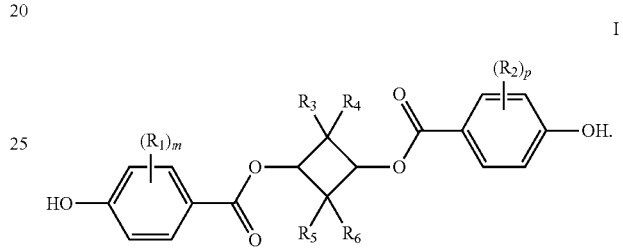

I

The process may include reacting a compound of Formula II

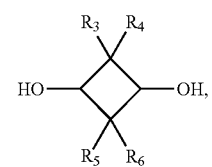

II with a compound of Formula III

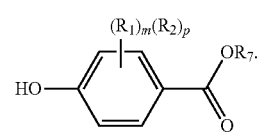

III

In particular embodiments, m and p may be the same or different and are each an integer from 0-4; each $R_1$ and $R_2$ are the same or different and are each independently selected from one or more of halogen, $C_1$-$C_{12}$ alkyl, $C_1$-$C_6$ aliphatic, $C_3$-$C_6$ cycloaliphatic, $C_1$-$C_{12}$ alkoxy, and $C_1$-$C_{12}$ alkyl ester; $R_3$, $R_4$, $R_5$, and $R_6$ are the same or different and are each independently selected from one or more of hydrogen, and $C_1$-$C_2$ aliphatic; and each $R_7$ is independently selected from hydrogen, $C_1$-$C_8$ aliphatic, or an aromatic. In certain aspects, the process may be a solution process or a melt transesterification process. In some aspects, the compound of Formula II may be tetramethylcyclobutane diol, and the compound of Formula III may be methyl 4-hydroxybenzoate.

In some embodiments, the process may further including adding the compound of Formula III to a solution of the compound of Formula II, and adding a catalyst. In certain aspects, the solvent may be xylene. In yet other aspects, the catalyst may be dibutyltin oxide. In some aspects, the process may further include distilling out one or more of solvent, solvent-water azeotrope, solvent-alcohol and alcohol formed during the reaction.

In certain embodiments, the process may further include precipitating out the compound of Formula I. In some aspects, the precipitating out may include cooling the reaction mixture and adding 1,2-dichloroethane. In other aspects, the process may further include filtering the precipitated solid, washing with hot dichloroethane, and drying. In some embodiments, the filtered precipitated solid may be a compound of Formula I having a purity of at least about 97%.

In certain embodiments the process for preparing tetramethylcyclobutane diol-2,5-bis(4-hydroxybenzoate) of Formula Ia

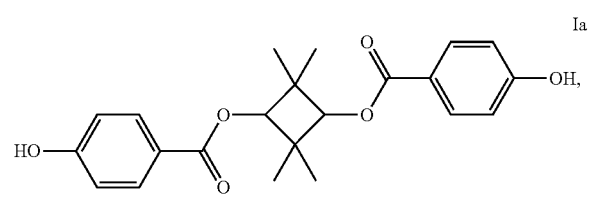

may include adding methyl 4-hydroxybenzoate to a solution of tetramethylcyclobutane diol, adding a catalyst, distilling out solvent and methanol formed during the reaction, and precipitating out the compound of Formula I. In some aspects, the solvent may be xylene. In other aspects, the catalyst may be dibutyltin oxide. In yet other aspects, the solvent may be xylene and the catalyst may be dibutyltin oxide.

In certain embodiments, a process is provided of purifying a mixture of a compound of Formula I. In certain aspects, the process may include dissolving a crude mixture in a suitable solvent, adding activated carbon to the mixture and heating, filtering and washing the mixture with hot solvent, and crystallizing the mixture. In some aspect, the process may further include cooling the crystallized mixture, and precipitating the solid by filtering, washing with solvent and drying. In particular aspects, the precipitated solid may be a compound of Formula I having a purity of at least about 99.3% after purification.

In some embodiments, an article of manufacture is provided including a polymer prepared from a composition containing the compound of Formula I. In other embodiments, an article of manufacture is provided including a polymer prepared from a composition containing the compound of Formula Ia. In certain embodiments, the articles may be an electronic device. In yet other embodiments, the article may include a polymer such as polycarbonate.

In other embodiments, a process is provided for preparing a tetramethylcyclobutane diol-2,5-bis(4-hydroxybenzoate) of the Formula Ia, comprising: adding methyl 4-hydroxybenzoate to a solution of tetramethylcyclobutane diol, adding a catalyst, distilling out solvent and methanol formed during the reaction, measuring the % areas of the monoester and diester in the reaction until the % area of diester is between 50% and 80% based on the areas of the monoester and diester being 100% as measured using high pressure liquid chromatography and precipitating out the compound of Formula I.

These and other non-limiting characteristics are more particularly described below.

DETAILED DESCRIPTION

The present disclosure may be understood more readily by reference to the following detailed description of desired embodiments and the examples included therein, and discussed in detail below.

In describing embodiments, specific terminology is employed for the sake of clarity. However, the disclosure is not intended to be limited to the specific terminology so selected. A person skilled in the relevant art will recognize that other equivalent components can be employed and other methods developed without departing from the broad concepts of the current disclosure. All references cited herein are incorporated by reference in their entirety as if each had been individually incorporated. Headings used herein are provided for clarity and organizational purposes only, and are not intended to limit the scope of the disclosure.

Numerical values in the specification and claims of this application, particularly as they relate to polymers or polymer compositions, reflect average values for a composition that may contain individual polymers of different characteristics. Furthermore, unless indicated to the contrary, the numerical values should be understood to include numerical values which are the same when reduced to the same number of significant figures and numerical values which differ from the stated value by less than the experimental error of conventional measurement technique of the type described in the present application to determine the value.

In the following specification including the claims which follow, reference will be made to a number of terms which shall be defined to have the following meanings.

The singular forms "a," "an," and "the" include plural referents unless the context clearly dictates otherwise. All ranges disclosed herein are inclusive of the recited endpoint and independently combinable (for example, the range of "from 2 grams to 10 grams" is inclusive of the endpoints, 2 grams and 10 grams, and all the intermediate values).

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "integer" means a whole number and includes zero. For example, the expression "n is an integer from 0 to 4" means n may be any whole number from 0 to 4, including zero.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, the aldehyde group —CHO is attached through the carbon of the carbonyl group.

The terms "aliphatic" and "alkyl" refer to a linear or branched array of atoms that are not cyclic, have a valence of at least one, and have at least one carbon atom. The array of atoms may include single bonds, double bonds, or triple bonds (typically referred to as alkane, alkene, or alkyne). Alkyl groups may be substituted or unsubstituted. Examples of substituent groups include halogen, alkoxy, alkanoyl, mercapto groups, ester, amino, amide, nitro, nitrile, alkoxycarbonyl, carboxyl, hydroxyl, thiol, aryloxy or carbonyl. The array of atoms may include heteroatoms such as nitrogen, sulfur, silicon, selenium and oxygen or may be composed exclusively of carbon and hydrogen. Exemplary aliphatic groups include, but are not limited to, methyl, ethyl, isopropyl, isobutyl, chloromethyl, hydroxymethyl (—CH$_2$OH), mercaptomethyl (—CH$_2$SH), methoxy, methoxycarbonyl (CH$_3$OCO—), nitromethyl (—CH$_2$NO$_2$), and thiocarbonyl.

The term "aromatic" or "arylene group" refers to an array of atoms having a valence of at least one and comprising at least one aromatic group. The array of atoms may include heteroatoms such as nitrogen, sulfur, selenium, silicon and oxygen, or may be composed exclusively of carbon. The aromatic group may also include nonaromatic components. For example, a benzyl group is an aromatic group that comprises a phenyl ring (the aromatic component) and a methylene group (the nonaromatic component). Exemplary aromatic groups include, but are not limited to, phenyl, pyridyl, furanyl, thienyl, naphthyl, biphenyl, 4-trifluoromethylphenyl, 4-chloromethylphen-1-yl, and 3-trichloromethylphen-1-yl (3-CCl$_3$Ph-).

The term "cycloalkyl" refers to an array of atoms which is cyclic but which is not aromatic. The cycloaliphatic group may include heteroatoms such as nitrogen, sulfur, selenium, silicon and oxygen, or may be composed exclusively of carbon and hydrogen. A cycloaliphatic group may comprise one or more noncyclic components. For example, a cyclohexylmethyl group (C$_6$H$_{11}$CH$_2$) is a cycloaliphatic functionality, which comprises a cyclohexyl ring (the array of atoms which is cyclic but which is not aromatic) and a methylene group (the noncyclic component). Exemplary cycloaliphatic groups include, but are not limited to, cyclopropyl, cyclobutyl, 1,1,4,4-tetramethylcyclobutyl, piperidinyl, and 2,2,6,6-tetramethylpiperydinyl.

The term "halogen" refers to F, Br, Cl and I. In some embodiments, halogen can be Br or Cl.

In describing the various embodiments below, it should be understood that any recited substituents for a particular embodiment can be combined with any other substituents from other embodiments.

In exemplary embodiments, the compound of the present disclosure may be a compound of Formula I

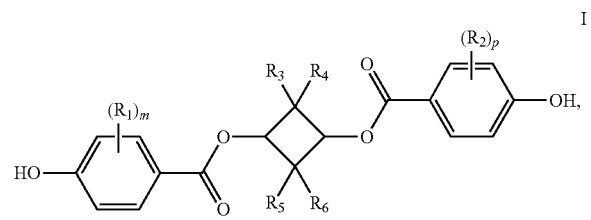

wherein m and p may be the same or different and are each an integer from 0-4; each R$_1$ and R$_2$ are the same or different and are each independently selected from one or more of halogen, C$_1$-C$_{12}$ alkyl, C$_1$-C$_6$ aliphatic, C$_3$-C$_6$ cycloaliphatic, C$_1$-C$_{12}$ alkoxy, and C$_1$-C$_{12}$ alkyl ester; and R$_3$, R$_4$, R$_5$, and R$_6$ are the same or different and are each independently selected from one or more of hydrogen, and C$_1$-C$_2$ aliphatic. That is, each aromatic ring bearing R$_1$ and R$_2$ may have no substituents or can include up to four substituents, each of which may be the same or different. The two aromatic rings may have the same or different substitution patterns.

In some embodiments, R$_1$ and R$_2$ are the same or different and are each independently selected from one or more of halogen, C$_1$-C$_6$ alkyl, C$_3$-C$_6$ cycloaliphatic, C$_1$-C$_6$ alkoxy, and C$_1$-C$_6$ alkyl ester; and R$_3$, R$_4$, R$_5$, and R$_6$ are the same or different and are each independently selected from one or more of hydrogen, and C$_1$-C$_2$ aliphatic. In some embodiments, m and p are zero, and R$_3$, R$_4$, R$_5$, and R$_6$ are each methyl. In any embodiment, m and p can be 1 or 2.

In some embodiments, R$_1$ and R$_2$ are the same or different and are each independently selected from one or more of halogen, C$_1$-C$_{12}$ alkyl, C$_3$-C$_6$ cycloaliphatic, C$_1$-C$_{12}$ alkoxy and C$_1$-C$_{12}$ alkyl ester; and R$_3$, R$_4$, R$_5$, and R$_6$ are the same or different and are each independently selected from one or more of hydrogen, and C$_1$-C$_2$ alkyl.

In some embodiments, R$_3$ and R$_5$ are hydrogen, and R$_4$ and R$_6$ are methyl or ethyl. In some embodiments, none of R$_3$, R$_4$, R$_5$, and R$_6$ is hydrogen. In exemplary embodiments, R$_3$, R$_4$, R$_5$, and R$_6$ are the same or different and are each independently hydrogen, methyl or ethyl.

In exemplary embodiments, m is zero and p is non-zero, i.e., only one of the rings bearing R$_1$ (or R$_2$) is substituted, and in other exemplary embodiments, m and p are both zero, i.e., neither ring bearing R$_1$ (or R$_2$) is substituted. In other exemplary embodiments, R$_1$ and R$_2$ can be the same or different and are each independently halogen, C$_1$-C$_6$ alkyl, methoxy, ethoxy of C$_1$-C$_6$ alkyl ester. In some embodiments, R$_1$ and R$_2$ are halogen, methyl or ethyl. In embodiments, R$_1$ and R$_2$ may be C$_1$-C$_{12}$ alkyl, aryl alkyl, or a halogen such as chlorine, bromine, or iodine.

In particular embodiments, the compound may be derived from a cyclobutane diol. In a specific embodiment, the compound is tetramethylcyclobutane diol-2,5-bis(4-hydroxybenzoate) ("TMCBD-BP") having the structure Ia:

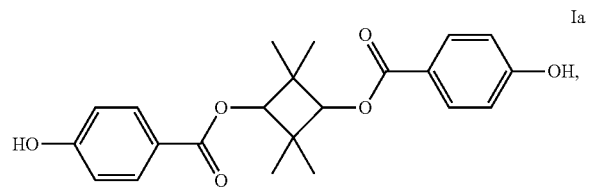

In another embodiment, the present disclosure is a process for preparing a compound of Formula I

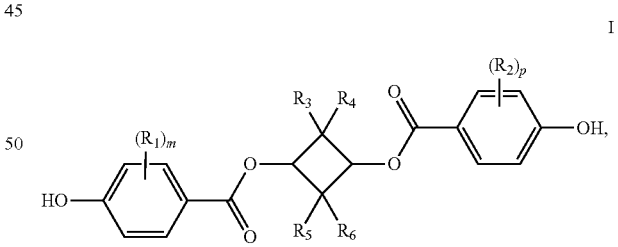

comprising reacting a compound of Formula II

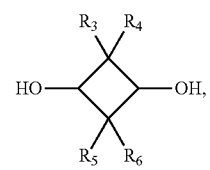

with a compound of Formula III

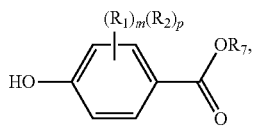

where the compound of Formula III may represent a single compound of Formula IIIa, i.e.,

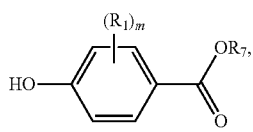

or a compound of Formula IIIa and a compound of Formula IIIb,

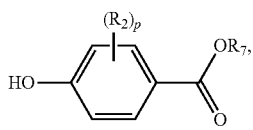

wherein m and p are the same or different and each is an integer from 0-4; $R_1$ and $R_2$ are the same or different and are each independently selected from one or more of halogen, $C_1$-$C_{12}$ alkyl, $C_1$-$C_6$ aliphatic, $C_3$-$C_6$ cycloaliphatic, $C_1$-$C_{12}$ alkoxy, and $C_1$-$C_{12}$ alkyl ester; $R_3$, $R_4$, $R_5$, and $R_6$ are the same or different and are each independently selected from one or more of hydrogen, and $C_1$-$C_2$ aliphatic; and each $R_7$ is independently selected from hydrogen, $C_1$-$C_8$ aliphatic, or an aromatic group. In the case where both a compound of IIIa and a compound of Formula IIIb are used, each $R_7$ may be the same or different.

In some embodiments, $R_1$, $R_2$, $R_3$, $R_4$, $R_5$, and $R_6$ are defined above, and each $R_7$ is independently selected from hydrogen, $C_1$-$C_8$ aliphatic, or an aromatic group. The aromatic group may be a substituted aromatic, such as a phenol. The phenol may be substituted. The aromatic group may be substituted with a hydroxyl, alkoxy, alkoxycarbonyl, arylalkyl, halogen, sulfide, sulfate, nitrate, amino, nitrile, and/or nitro group. The aromatic compound may contain alkyl substituents of one or more carbon atoms per alkyl substituent. The aromatic group may be mono-nuclear or poly-nuclear and may contain one or more alkyl substituents. For example, the second reactant may be a mono-, di-, tri, or tetra-alkyl substituted aromatic hydrocarbon, such as a dimethylbenzene, trimethylbenzene, dimethylnaphthalene, trimethylnaphthalene, tetramethylnaphthalene, diethylbenzene, mono-methylbenzene, monoethylbenzene, monomethylnaphthalene, diethylnaphthalene, methylphenanthrene, dimethyl anthracene, dimethylpyrene, tetraethyl phenanthrene, dimethylchrysene, tetraethyl pyrene, trimethyl anthracene, diethyl-dimethyl phenanthrene, methyl ethylbenzene, methyl ethyl naphthalene, and the like. The alkyl substituent may have 2 or more carbon atoms. The aromatic compound may be heterocyclic. In some embodiments $R_7$ is an aryl, alkyl or tolyl group. In exemplary embodiments, $R_7$ is $C_1$-$C_4$ alkyl or benzyl. $R_1$ and $R_2$ may be present or absent and may be the same or different.

In embodiments where only a compound of Formula IIIa is used to make the diester product of Formula I, i.e., where $(R_1)_m=(R_2)_p$, the compound of Formula III may be present in a range of about 2-10 molar equivalents with respect to compound with Formula II. In embodiments, the range may be about 2-5 molar equivalents or about 3-4 molar equivalents.

In embodiments adding compounds to compounds of Formulas IIIa and IIIb, the two compounds can be added in varying stepwise manner. By conducting the reaction in a stepwise manner, one may obtain the final product with different $R_1$ and $R_2$. This may also be done by varying the molar ratios of compounds of Formulas IIIa and IIIb relative to the compound of Formula II.

In some embodiments, to make a compound of Formula I with different $R_1$ and $R_2$, the reaction is first carried out between a compound of Formula II and a compound of Formula IIIa in a molar equivalent ratio of 1:0.5 to obtain a monoester of Formula IV,

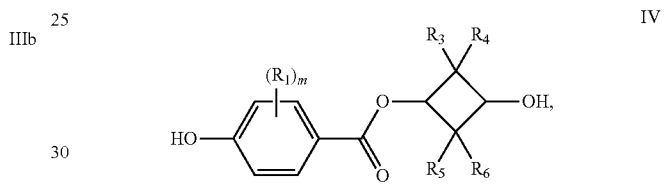

wherein $R_1$, $R_3$, $R_4$, $R_5$, and $R_6$ are defined above. In some embodiments with particular compounds of Formula III, one may obtain a greater portion of the diester of Formula I as a product. Any diester that is formed, as well as any unreacted diol, can be removed before further reaction. Then the monoester of Formula IV may be reacted with Formula IIIb in the molar equivalent ratio of 1:0.5 to provide the final product. The resulting mixture may contain both di- and mono-esters, and can be subjected to further purification to provide the desired product.

In particular embodiments, the compound of Formula III may have a pKa value such that, when reacted with the compound of Formula II, a bisphenol is produced that has a pKa value of between 8 and 11. The compound of Formula III may be methyl 4-hydroxybenzoate.

In some embodiments, the compound of Formula II is tetramethylcyclobutane diol. In this and other embodiments, the compound of Formula III is methyl 4-hydroxybenzoate.

The compound of Formula I can be manufactured by processes such as esterification or transesterification. Although many methods of preparing compounds of Formula I are known, for example, solution, interfacial, melt esterification or transesterification, or solid state esterification or transesterification.

For example, the compound of Formula I may be made under melt transesterification conditions. Generally, in melt esterification, temperature conditions and the presence of the transesterification catalyst and, optionally, a specific solvent, drive the formation of the product. More specifically, the compound of Formula I may be prepared by reacting molten compound of Formula II with the compound of Formula III in the presence of a transesterification catalyst. The reactants and transesterification catalyst may be combined in any order in a mixer or extruder to form a dispersion or slurry. The dispersion may then be refluxed with a solvent and then cooled to precipitate the desired product of the compound of Formula I.

In exemplary embodiments, the process provides combining the compound of Formula III, the compound of Formula II, a solvent and a catalyst. The catalyst may be added before or after the combining other components. In some embodiments, the compound of Formula II is dissolved in a solvent prior to the addition of the compound of Formula III. The compound of Formula III can then be added as a solution. The compound of Formula II, optionally in a solution, can be added to the compound of Formula III, optionally in a solution. In exemplary embodiments, $R_1$ and $R_2$ are the same and at least two molar equivalents of the compound of Formula III are combined with the compound of Formula II.

In some embodiments, the reaction is carried out in a solvent that may be any suitable solvent, such as an organic solvent, for example, an aromatic solvent. The solvent may be hydrocarbons, such as o-dichlorobenzene, chlorobenzene, xylene, hexane, benzene, cyclohexane, toluene, 1,2-dichloroethane, ethyl acetate, a mixture of two or more solvents, such as ethyl acetate and hexane. The mixture may be in any proportion, for example, a 50:50 (by weight or by volume) mixture. The organic solvent may have at least 1 carbon atom and 1 hydrogen atom, have a low molecular weight, and exist in liquid form at room temperature. The solvent may be an aliphatic-chain compound, such as n-hexane. The solvent may be an aromatic compound with a 6-carbon ring, such as benzene or xylene. The aliphatic or aromatic solvent may contain a halogen substituent and may be a halogenated hydrocarbon, such as perchloroethylene (PCE or PER), trichloroethylene (TCE), and carbon tetrachloride. Alcohols, ketones, glycols, esters, ethers, aldehydes, and pyridines may be substituted for hydrogen. In specific embodiments, the solution comprises the solvent xylene.

The catalyst, e.g., a melt transesterification catalyst, may be one or more of titanium isopropoxide, a hydroxide of an alkali metal, a hydroxide of an alkaline earth metal, an alkali metal salt, an alkaline earth metal salt, a quaternary ammonium salt of boron hydride, a quaternary ammonium salt of aluminum hydride, a hydride of an alkali metal, a hydride of an alkaline earth metal, an aryloxide of an alkali metal, an aryloxide of an alkaline earth metal, an organic salt of an alkali metal, an organic salt of an alkaline earth metal, a boron compound, a silicon compound, a germanium compound, a tin compound, an organotin compound, a lead compound, an onium compound, an antimony compound, a manganese compound, a titanium compound, a zinc compound or a zirconium compound.

The hydroxide of an alkali metal or an alkaline earth metal may be lithium hydroxide, sodium hydroxide, potassium hydroxide or calcium hydroxide. The quaternary ammonium salts of boron hydride and of aluminum hydride may be lithium aluminum hydride, sodium boron hydride and tetramethyl ammonium boron hydride. The hydrides of an alkali metal and of an alkaline earth metal may be lithium hydride, sodium hydride or calcium hydride. The alkoxides of an alkali metal and of an alkaline earth metal may be lithium methoxide, sodium ethoxide or calcium methoxide. The aryloxides of an alkali metal and of an alkaline earth metal may be lithium phenoxide, sodium phenoxide, magnesium phenoxide, LiO—Ar—OLi, wherein Ar represents an arylene group, and NaO—Ar—ONa, wherein Ar represents an arylene group. The organic salts of an alkali metal and of an alkaline earth metal may be lithium acetate, calcium acetate or sodium benzoate. The zinc compounds may be zinc oxide, zinc acetate or zinc phenoxide. The boron compounds may be boron oxide, boric acid, sodium borate, trimethyl borate, tributyl borate, triphenyl borate, ammonium borate or phosphonium borate. The silicon compounds may be silicon oxide, sodium silicate, tetraalkylsilicon, tetraarylsilicon or diphenyl-ethyl-ethoxysilicon. The germanium compounds may be germanium oxide, germanium tetrachloride, germanium ethoxide or germanium phenoxide. The tin compounds may be tin oxide, dialkyltin oxide, dibutyltin oxide, dialkyltin carboxylate or tin acetate. The tin compounds that have an alkoxy group or an aryloxy group bonded to tin may include ethyltin tributoxide and organotin compounds. Lead compounds include lead oxide, lead acetate, lead carbonate and basic lead carbonate. Alkoxides and aryloxides of lead or organolead may also be used as a metal transesterification catalyst. Onium compounds may include quaternary ammonium salt, quaternary phosphonium salt, or a quaternary arsonium salt. The antimony compounds may include antimony oxide and antimony acetate. The manganese compounds may include manganese acetate, manganese carbonate and manganese borate. The titanium compounds include titanium oxide and titanium alkoxides and titanium aryloxide. The zirconium compounds include zirconium acetate, zirconium oxide, zirconium alkoxide, zirconium aryloxide, and zirconium acetylacetone.

In addition to the foregoing, transesterification catalysts used herein may include tetrabutylammonium hydroxide, methyltributylammonium hydroxide, tetrabutylammonium acetate, tetrabutylphosphonium hydroxide, tetrabutylphosphonium acetate, and/or tetrabutylphosphonium phenolate. The transesterification catalyst as used herein may be one or more of the foregoing compounds. In specific embodiments, the catalyst is dibutyltin oxide.

The process may include heating the solution to elevated temperatures for specific durations. Appropriate temperature ranges include at least above room temperature, up to the reflux temperature of any solvent present, about 140° C. to 220° C., or about 160° C. to 180° C. The solution may be heated for a period of time sufficient to produce a diester, for example, about 8 hours to about 24 hours. For example, after the step of adding the compound of Formula II to the solvent, the temperature of the solution may be increased gradually to about 150° C. during the addition of the compound of Formula III. In some embodiments, the solution mixture is heated to 180° C. after addition of catalyst. The temperature and duration may depend on the solution conditions and quality as well as reaction rate. In a particular embodiment, the solution should be heated or stirred until the components are fully solubilized and visually clear. A person skilled in the art applying typical conditions can readily optimize reaction times and temperatures in view of the present description.

The reaction time may be determined based upon the conversion of monoester to diester i.e. selectivity of the desired bisphenol to monoester and to the formation of oligomers. In embodiments, the reaction is stopped when the selectivity of the diester in respect to the monoester is about 80%, (i.e. about 80% diester and about 20% monoester based on the combination of % areas for the mono and diester of butane diol being about 100%). Longer reaction times can lead to an increase in the formation of oligomers at the expense of the desired product. In one embodiment the selectivity is between 50% and 85%, in another embodiment the selectivity is between 50% and 80% in another embodiment the selectivity is between 60% and 85% and in another embodiment the selectivity is between 60% and 80%, and in another embodiment the selectivity is about 80%, in another embodiment the selectivity is about 75% and in another embodiment the selectivity is about 70%.

In some embodiments, the process includes distilling out the solvent and other components, e.g., the xylene, alcohol, solvent-water azeotrope or solvent-alcohol azeotrope, formed during the reaction. Advantageously, in exemplary embodiments, as the solvent and byproducts are removed by, for example distillation, the compound of Formula I precipitates from the solution. The product, i.e., the compound of Formula I, can therefore be readily isolated from the reaction medium. In exemplary embodiments, the compound of Formula I can be isolated in purities of great than 90%, greater than 95% or greater than 97% after precipitation and washing. Yield at this stage can be 80% or higher.

There are a number of manners for precipitating out the compound of Formula I. For example, in specific embodiments, the process of precipitating out the compound of Formula I by cooling the reaction mixture to a lower temperature, e.g., about 100° C. (internal temperature), and a adding a solvent, e.g., hydrocarbon. In some embodiments, the solvent may be one or more of chloroform, dichloromethane, dichloroethane, chloroalkanes, chlorobenzene, ortho-dichlorobenzene (ODCB), toluene, xylene or benzene. In certain embodiments, the solvent is dichloroethane. In other embodiments, the solvent is about 150 ml of 1,2-dichloroethane (DCE). In some embodiments, the process includes filtering, washing with hot dichloroethane, and drying the precipitated solid.

In another embodiment, the present disclosure provides a method of purifying a mixture of a compound of Formula I. In specific embodiments, the method includes dissolving a crude mixture in a suitable solvent such as, for example an alcohol or ester, such as ethyl acetate (EtOAc); adding activated carbon or charcoal to the mixture and heating; filtering and washing the mixture with hot solvent, and crystallizing the compound of Formula I from the mixture. In some embodiments, the amount of charcoal added may be about 5-20 wt %, 5-10 wt %, or about 10 wt %.

In some embodiments, the method further includes cooling the crystallized mixture; and precipitating the solid by filtering, washing with solvent and drying. In particular embodiments the precipitated solid may be a compound of Formula I having a purity of at least about 99.3%. In some embodiments, the yield may be about 40 to 90%. In other embodiments, the purity is about 99 to 99.9%

The compounds of the present disclosure may be used to make polymers. Methods of using the compound of Formula I are described in co-pending U.S. patent application Ser. No. 13/155,065, entitled "Polycarbonate Polymers Containing Bisphenol Compounds", in the name of Jean-Francois Morizur, filed simultaneously herewith, and incorporated by reference in its entirety.

The compounds and compositions may further include other additives which can be incorporated with polymeric compositions, with the proviso that the additives are selected so as not to adversely affect the desired properties of the compound or polymer. Mixtures of additives may be used. Such additives may be mixed at a suitable time during the mixing of the components. Examples of such additives include fillers, antioxidants, heat stabilizers, light stabilizers, plasticizers, lubricants, antistatic agents, flame retardants, impact modifiers, and anti-drip agents. Additives may be added to the compounds of the invention or the blend generated with other compounds to make subject polymers.

The compounds and compositions described herein may be incorporated into various articles of manufacture. For example, the compounds and compositions may be polymerized, alone or together with other monomeric species. For example, the polymer may be polyurethane, polyurea, polyarylate, polyester, polyether, polyetheramide, polyformyl, or polyphenylene ether, each of which may be a homopolymer or a copolymer, or a polymer that includes segments thereof. The polymers incorporating compounds of the present disclosure are suitable for use in molding articles to provide shaped articles. The shaped articles can be compression molded, injection molded, blow molded, injection-blow-molded, or extruded. The article can be a solid sheet, an extruded multi-wall sheet, a cast film, or an extruded film. The article can also be a multi-layered article where the outer layer is made from the polymer. Such multi-layered articles include a co-extruded solid sheet, a co-extruded multi-wall sheet, a co-extruded film, or a film cast onto a separately molded part. Alternatively, the multi-layered article may be made by molding a different composition or resin onto a film made from the polymer. Examples of such applications include TV and notebook bezels. Multi-layer articles may be used in mobile phones and other consumer electronic products.

In one embodiment, the article of manufacture comprises a polymer prepared from a composition, for example a resin, containing the compound of Formula I

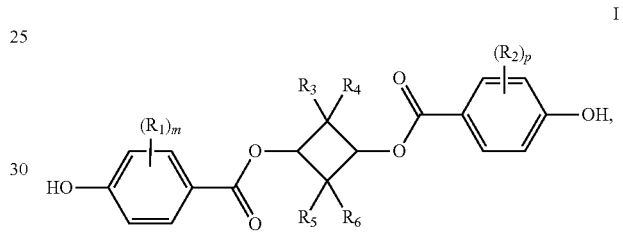

wherein m and p may be the same or different and are each an integer from 0-4; each $R_1$ and $R_2$ are the same or different and are each independently selected from one or more of halogen, $C_1$-$C_{12}$ alkyl, $C_1$-$C_6$ aliphatic, $C_3$-$C_6$ cycloaliphatic, $C_1$-$C_{12}$ alkoxy, and $C_1$-$C_{12}$ alkyl ester; and $R_3$, $R_4$, $R_5$, and $R_6$ are the same or different and are each independently selected from one or more of hydrogen, and $C_1$-$C_2$ aliphatic.

In a further embodiment, the article is an electronic device.

In another embodiment, the article of manufacture comprises a polymer prepared from a composition, for example a resin, containing the compound of Formula Ia

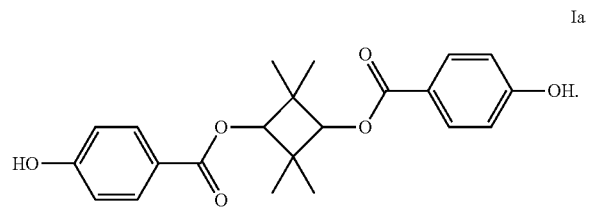

In a further embodiment, the article is an electronic device.

EXAMPLES

The examples listed below are illustrative and are not intended to limit the scope of the present disclosure.

Example 1

Synthesis of tetramethylcyclobutane diol-2,5-bis(4-hydroxybenzoate) (TMCBD-BP) (Formula Ia) from methyl 4-hydroxybenzoate 40.0 g (0.277 mol.) of TMCBD was taken in a 2-necked round bottom fitted with a nitrogen inlet and a distillation condenser. To this 200 ml of xylene was added. The bath temperature was slowly increased to 150° C. during which 168.0 g (1.21 mol.) of methyl 4-hydroxybenzoate was added. The reaction mixture was thoroughly mixed and the bath temperature was gradually increased to 180° C. during which, 2.76 g (0.0077 mol.) of dibutyltin oxide was added. The reaction mixture was kept with stifling at that temperature for 22 hours, while distilling out xylene and methanol formed during the reaction. The reaction was stopped when the selectivity of TMCBD-BP with respect to the monoester was about 80%, (i.e. about 80% diester and about 20% monoester based on the combination of % areas for the mono and diester of butane diol being about 100%), beyond which continuing the reaction would lead to increase in the formation of oligomers. Selectivity towards the desired product was monitored by high performance liquid chromatography (HPLC). Reaction progress was monitored by measuring the area % of the mono ester and diester of TMBCD using high pressure liquid chromatography (HPLC). The solvent system used for HPLC analysis was acetonitrile/water (with 0.02% phosphoric acid) with gradient elution using C18, 15 cm, 5 micron column & detection at 254 nm. The reaction mixture was then cooled to 100° C. (internal temperature) following which 150 ml of 1,2-dichloroethane was added and the mixture was refluxed for 3 hours when the desired product precipitates out. The reaction mixture was then cooled to room temperature and made to stand for 4 hours at room temperature for complete precipitation of the desired product. The precipitated solid was filtered, washed thoroughly with hot dichloroethane (~200 ml) and dried. 38.0 g of off-white solid with purity 97% (determined by HPLC area %) was obtained.

The crude material obtained was further purified by crystallization in the next Example.

Example 2

Purification of tetramethylcyclobutane diol-2,5-bis(4-hydroxybenzoate) (TMCBD-BP) (Formula Ia)

35.0 g of the crude material from Example 1 was refluxed (to dissolve) in 350 ml of EtOAc. To this, 3.5 g of activated charcoal was added and the mixture was heated to reflux for 1 hour. The charcoal was filtered and washed thoroughly with hot EtOAc (150 ml). The volume of the filtrate obtained was reduced in a rotary evaporator under vacuum to 2 wt/vol, (i.e., ~70 ml) when the desired product begins to crystallize. The mixture was allowed to stand at room temperature for about 5 hours. Complete crystallization of the desired product was ensured by cooling the material (to 0° C.) in ice for 2 hours. Precipitated solid was filtered, washed with ice cold EtOAc:Hexane (50:50) solvent mixture (1 wt./vol.) and dried.

28.0 g of the pure TMCBD-BP with purity 99.3% (determined by HPLC area %) was obtained. M.P.=275.2° C.; $^1$H NMR (DMSO-$d_6$, 300 MHz): δ 10.2 (s, 2H, Ar—OH), δ 7.8 (s, 4H, Ar—H), δ 6.8 (s, 4H, Ar—H), δ 4.6 (s, 2H, H—CO—), δ 1.2 (s, 12H, —$CH_3$); LC/MS: 383.8 (M-1).

Example 3

Synthesis of tetramethylcyclobutane diol-2,5-bis(4-hydroxybenzoate) (TMCBD-BP) (Formula Ia) from 4-hydroxybenzoic acid 5.0 g (0.035 mol.) of TMCBD, 14.38 g (0.104 mol.) of 4-hydroxybenzoic acid and 4.0 g sodium bisulphite (10 wt % of total reactants) were suspended in a mixture of 25 ml. Toluene and 1.0 ml of diethylene glycol dimethyl ether, and the mixture was heated to 108-110° C. with stifling. The water formed during the reaction was removed by azeotropic distillation, and the mixture was then cooled to 85° C., following which 45 ml. of ethylacetate was added. The organic layer was washed twice with saturated sodium bicarbonate solution (2×50 ml), followed by water (2×50 ml) and dried over anhydrous sodium sulphate. Ethylacetate was removed by distillation under vacuum. To the residue obtained 10 ml of toluene was added and the mixture was refluxed for 1 hour, and then allowed to cool to room temperature. The precipitated solid was filtered, washed thoroughly with hot toluene (20 ml) and dried. 1.7 g of black solid with purity 87% (HPLC area %) was obtained.

This crude material was not subject to further purification.

The embodiments illustrated and discussed in this specification are intended only to teach those skilled in the art the best way known to the inventors to make and use the invention. Nothing in this specification should be considered as limiting the scope of the present disclosure. All examples presented are representative and non-limiting. The above-described embodiments of the disclosure may be modified or varied, without departing from the invention, as appreciated by those skilled in the art in light of the above teachings. It is therefore to be understood that, within the scope of the claims and their equivalents, the invention may be practiced otherwise than as specifically described.

We claim:
1. A compound of Formula I

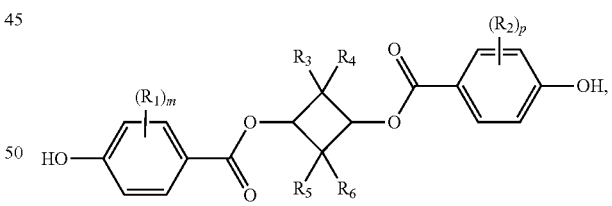

wherein m and p may be the same or different and are each an integer from 0-4; each $R_1$ and $R_2$ are the same or different and are each independently selected from one or more of halogen, $C_1$-$C_{12}$ alkyl, $C_1$-$C_6$ aliphatic, $C_3$-$C_6$ cycloaliphatic, $C_1$-$C_{12}$ alkoxy, and $C_1$-$C_{12}$ alkyl ester; and $R_3$, $R_4$, $R_5$, and $R_6$ are the same or different and are each independently selected from one or more of hydrogen, and $C_1$-$C_2$ aliphatic.

2. The compound of claim 1, wherein m is 1.
3. The compound of claim 1, wherein p is 1.
4. The compound of claim 1 wherein m and p are 0.
5. The compound of claim 1, wherein $R_3$, $R_4$, $R_5$, and $R_6$ are each methyl.

6. A compound of Formula Ia

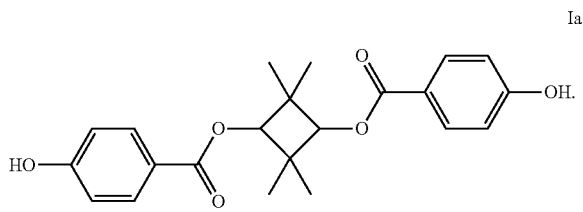

7. A process for preparing a compound of Formula I

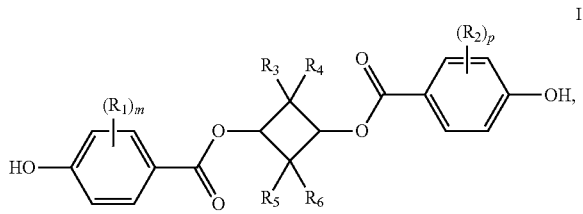

comprising reacting a compound of Formula II

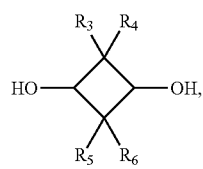

with a compound of Formula III

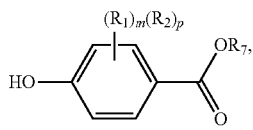

wherein m and p may be the same or different and are each an integer from 0-4;

each $R_1$ and $R_2$ are the same or different and are each independently selected from one or more of halogen, $C_1$-$C_{12}$ alkyl, $C_1$-$C_6$ aliphatic, $C_3$-$C_6$ cycloaliphatic, $C_1$-$C_{12}$ alkoxy, and $C_1$-$C_{12}$ alkyl ester;

$R_3$, $R_4$, $R_5$, and $R_6$ are the same or different and are each independently selected from one or more of hydrogen, and $C_1$-$C_2$ aliphatic; and each $R_7$ is independently selected from hydrogen, $C_1$-$C_8$ aliphatic, or an aromatic.

8. The process of claim 7, wherein the process is a solution process.

9. The process of claim 7, wherein the process is a melt transesterification process.

10. The process of claim 7, wherein the compound of Formula II is tetramethylcyclobutane diol.

11. The process of claim 7, wherein the compound of Formula III is methyl 4-hydroxybenzoate.

12. The process of claim 7, comprising:
    (a) adding the compound of Formula III to a solution of the compound of Formula II, and
    (b) adding a catalyst.

13. The process of claim 12, wherein the solvent comprises xylene.

14. The process of claim 12, wherein the catalyst is dibutyltin oxide.

15. The process of claim 12, further comprising distilling out one or more of solvent, solvent-water azeotrope, solvent-alcohol and alcohol formed during the reaction.

16. The process of claim 7, further comprising precipitating out the compound of Formula I.

17. The process of claim 16, wherein precipitating out comprising cooling the reaction mixture and adding 1,2-dichloroethane.

18. The process of claim 16, further comprising filtering the precipitated compound of Formula I, washing with hot dichloroethane, and drying.

19. The process of claim 16, wherein the filtered precipitated solid comprises a compound of Formula I having a purity of at least about 97%.

20. A process for preparing a tetramethylcyclobutane diol-2,5-bis(4-hydroxybenzoate) of the Formula Ia

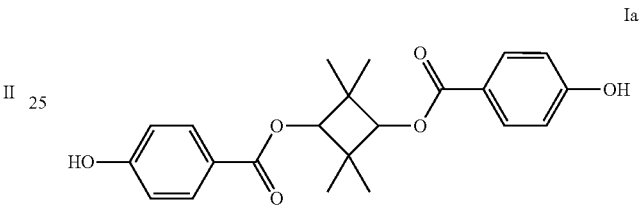

comprising:
    (a) adding methyl 4-hydroxybenzoate to a solution of tetramethylcyclobutane diol,
    (b) adding a catalyst,
    (c) distilling out solvent and methanol formed during the reaction, and
    (d) precipitating out the compound of Formula I.

21. The process of claim 20, wherein the solvent comprises xylene.

22. The process of claim 20, wherein the catalyst is dibutyltin oxide.

23. The process of claim 20, wherein the solvent comprises xylene and the catalyst is dibutyltin oxide.

24. A process of purifying a mixture of a compound of Formula I.

25. The process of claim 24, comprising:
    (a) dissolving a crude mixture in a suitable solvent;
    (b) adding activated carbon to the mixture and heating;
    (c) filtering and washing the mixture with hot solvent; and
    (d) crystallizing the mixture.

26. The process of claim 25, comprising
    (a) cooling the crystallized mixture; and
    (b) precipitating the solid by filtering, washing with solvent and drying.

27. The process of claim 26, wherein the precipitated solid comprises a compound of Formula I having a purity of at least about 99.3% after purification.

28. An article of manufacture comprising a polymer prepared from a composition containing the compound of claim 1.

29. The article of claim 28 wherein said article is an electronic device.

30. An article of manufacture comprising a polymer prepared from a composition containing the compound of claim 6.

31. The article of claim 30 wherein said article is an electronic device.

32. The article of claim 28, wherein said polymer is a polycarbonate.

33. A process for preparing a tetramethylcyclobutane diol-2,5-bis(4-hydroxybenzoate) of the Formula Ia

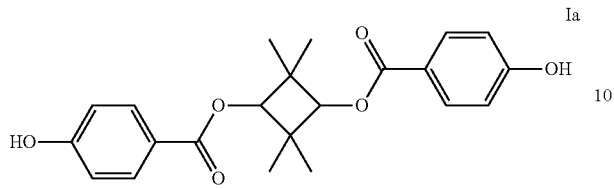

Ia comprising:
(a) adding methyl 4-hydroxybenzoate to a solution of tetramethylcyclobutane diol,
(b) adding a catalyst,
(c) distilling out solvent and methanol formed during the reaction,
(d) measuring the % areas of the monoester and diester in the reaction until the % area of diester is between 50% and 80% based on the areas of the monoester and diester being 100% as measured using high pressure liquid chromatography
(e) precipitating out the compound of Formula I.

* * * * *